United States Patent [19]
Sato et al.

[11] Patent Number: 5,550,284

[45] Date of Patent: Aug. 27, 1996

[54] PRODUCTION METHOD FOR ALKOXYNAPHTHALENECARBOXYLIC ACID

[75] Inventors: Toshio Sato; Ikuo Ito; Kazuhiko Maeda; Keiichi Yokota; Takeshi Namekata, all of Kashima-machi; Akihiko Nemoto, Okegawa, all of Japan

[73] Assignee: Sumikin Chemical Co., Ltd., Japan

[21] Appl. No.: 292,052

[22] Filed: Aug. 16, 1994

[30] Foreign Application Priority Data

Aug. 18, 1993 [JP] Japan .................................. 5-226453

[51] Int. Cl.$^6$ .................................................. C07C 63/34
[52] U.S. Cl. ...................... 562/467; 568/632; 568/659; 562/412; 562/413; 562/415
[58] Field of Search ................................ 562/467, 412, 562/413, 415; 568/632, 659

[56] References Cited

U.S. PATENT DOCUMENTS

| | | | |
|---|---|---|---|
| 3,371,111 | 2/1968 | Levy et al. | 562/467 |
| 3,803,245 | 9/1974 | Lodewijk | 562/467 |
| 4,374,262 | 2/1983 | McGinnis | 562/467 |
| 4,560,794 | 12/1985 | Foster | 562/467 |

*Primary Examiner*—Paul J. Killos
*Attorney, Agent, or Firm*—Harris Beach & Wilcox

[57] ABSTRACT

Alkoxynaphthalenecarboxylic acid is produced by a process comprising the addition of 1,3-butadiene to alkoxyalkylbenzene to yield an adduct. The adduct is cyclized in the presence of an acid catalyst to alkoxyalkyltetralin. The tetralin derivative is then dehydrogenated to produce aloxyalkylnaphthalene, which is oxidized to alkoxynaphthalenecarboxylic acid.

15 Claims, No Drawings

PRODUCTION METHOD FOR ALKOXYNAPHTHALENECARBOXYLIC ACID

BACKGROUND OF THE INVENTION

This invention relates to a novel method of producing alkoxynaphthalenecarboxylic acid. Hydroxynaphthalenecarboxylic acid, which is either alkoxynaphthalenecarboxylic acid or a reaction product formed during the dealkylation of alkoxynaphthalenecarboxylic acid, has been used widely as an intermediate raw material in different fields of medicine, agricultural chemicals, resin materials, electronic materials and the like.

As a production method of hydroxynaphthalenecarboxylic acid, the Kolbe-Schmitt process has been widely used for a long time. This is a well-known method by which the compound is synthesized by virtue of heating a naphtholates salt and carbon dioxide under pressure.

However, the aforementioned method employed in producing hydroxynaphthalenecarboxylic acid by the Kolbe-Schmitt process applied to naphthol has disadvantages, among which is the fact that the number of synthesizable isomers is limited.

It is, therefore, an object of the present invention to provide a novel method for producing alkoxynaphthalenecarboxylic acid which is a precursor of hydroxynaphthalenecarboxylic acid. Alkoxynaphthalenecarboxylic acid is among the isomers that are very hard to synthesize using the Kolbe-Schmitt process with naphthol.

As a result of continuous and diligent efforts on research and experiments to synthesize alkoxynaphthalenecarboxylic acid which is not feasibly synthesized by the Kolbe-Schmitt process using naphthol, the present inventors have found that the addition reaction of 1,3-butadiene to alkoxyalkylbenzene was not known, while on the other hand the addition reaction of 1,3-butadiene to alkylbenzene usually in the presence of alkaline metallic catalysts is known. The addition reaction of 1,3-butadiene to alkoxyalkylbenzene can be considered as a known addition reaction of olefin to the alkyl group of an alkylaromatic hydrocarbon having a benzylic hydrogen. Furhtermore, the present inventors had come to the findings that (1) alkoxylalkyltetralin can be prepared through the reactions of adding 1,3-butadiene to alkoxyalkylbenzene followed by cyclization, (2) alkoxyalkylnaphthalene can be produced by the dehydrogenation reaction of alkoxyalkyltetralin, and (3) alkoxynaphthalenecarboxylic acid can be obtained through the oxidation of the alkoxyalkylnaphthalene.

The first aspect of the present invention relates to a production process for alkoxyalkyltetralin which comprises, in the presence of the alkali metal catalysts essential for the reaction to take place, a step of adding 1,3-butadiene to alkoxyalkylbenzene, and a step wherein an adduct is subjected to cyclization in the presence of acid catalysts to yield alkoxyalkyltetralin.

Furthermore, a second aspect of the present invention relates to a production process which comprises, in the presence of alkali metal catalysts, a step of adding 1,3-butadiene to alkoxyalkylbenzene, a step wherein additives are subjected to cyclization in the presence of acid catalysts to produce alkoxyalkyltetralin, and a step of dehydrogenating the alkoxyalkyltetralin to alkoxyalkylnaphthalene.

Moreover, a third aspect of the present invention relates to a production method which comprises, in the presence of alkali metal catalysts, a step of adding 1,3-butadiene to alkoxyalkylbenzene, a step of subjecting an adduct to cyclization in the presence of acid catalysts to produce alkoxyalkyltetralin, and a step of dehydrogenating the alkoxyalkyltetralin to be converted to alkoxyalkylnaphthalene and the step of oxidizing said alkoxyalkylnaphthalene to yield alkoxynaphthalenecarboxylic acid.

Alkoxyalkylbenzene, which is expressed in the general formula as shown below, is the starting raw material of choice employed in the present invention. It is converted to a final product comprising alkoxynaphthalenecarboxylic acid:

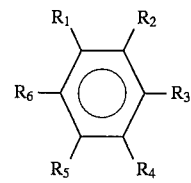

where $R_1$ is an alkyl group having a benzylic hydrogen: and $R_2$-$R_6$ are H, alkyl, phenyl, alkoxy or phenoxy.

Either $R_2$ or $R_6$ is H, and at least one of $R_2$-$R_6$ should be alkoxy or phenoxy.

An addition reaction of 1,3-butadiene to alkoxyalkylbenzene can proceed through anion mediation, so that any type of compound which generates an active species can act as an anionic addition catalyst. In general, sodium, potassium or cesium, an alloy thereof or an organometallic compound thereof can be used. In other words, any type of alkali metal catalyst can be employed if it produces the condition to function effectively as an anionic addition catalyst.

In this case, if polycyclic aromatic compounds acting as promoters, in particular naphthalene, biphenyl, phenanthrene, anthracene or pyrene, or alkyl derivatives thereof, are introduced selectivity will be improved. Accordingly, a compound prepared in advance through a reaction of a polycyclic aromatic compound in the presence of alkali metal catalysts is utilized in the present invention.

When a chain ether compound or cyclic ether compound is admixed, the aforementioned addition reaction will exhibit an enhanced performance, since the catalyst is dissolved therein. Moreover, the addition reaction proceeded effectively at a relatively low temperature. This is an additional advantage or the present invention. Although diethyl ether, tetrahydrofuran or dioxane could be the chain or cyclic ether compounds, observed that tetrahydrofuran has been observed to be the most effective compound.

In general, for the addition reaction of 1,3-butadiene to alkoxyalkylbenzene regardless of the manner of reactions and order of addition, 1,3-butadiene is normally fed into liquid phase or gaseous phase of alkoxyalkylbenzene either under slightly reduced pressure, atmospheric pressure, or excess pressure. The addition reaction can be achieved by a batch process, semi-continuous process, continuous process.

If the reaction temperature for the addition reaction is too low the reaction rate will consequently be low; while on the other hand if it is too high selectivity will be reduced. An optimum reaction temperature generally lies in a range from room temperature upto approximately 140° C. However, there could be some cases in which the addition reaction is operated at above 140° C., depending upon the type of catalyst selected.

Although a solvent can be used for the addition reaction, it is advantageous to use the ether group solvent for the reasons mentioned above.

The amount of alkali metal catalysts required depends on the presence or absence of a promotor or a solvent. An amount of approximately 0.5–30 mol % of the alkali metal catalyst with respect to alkoxyalkylbenzene is suitable. If the alkali metal catalyst is added excessively, the reaction will proceed without complication but such practice is uneconomical. If sufficient catalyst is not added selectivity might be reduced.

The amount of promotor required may be in the range from 5 to 50 mol % for each mol of the alkali metal catalyst used. Addition of excessive promoter do not cause any problems; on the other hand insufficient promoter may reduce reaction efficiency.

If the amount of 1,3-butadiene is excessive di-adduct will be easily formed on the other hand, if too little, productivity will drop. Accordingly, the appropriate ratio of 1,3-butadiene should be approximately 0.3–0.7 mol per mol of alkoxyalkylbenzene.

In the addition reaction of 1,3-butadiene to alkoxyalkylbenzene, the 1:1 aduct is be first synthesized, and then separated by distillation, regardless of separation or the nonseparation of the catalyst. Although the position of the un-saturated bonding of said 1:1 adduct is not yet known, it can be speculated that it would be either the 1-position or the 2-position. In the case where a solvent such as tetrahydrofuran is used, the solvent can be separated and recovered at this stage of the reaction for recycling.

The 1:1 adduct which will be utilized in a cyclization reaction that follows the addition reaction does not need to be highly pure. The 1:1 adduct including unreacted alkoxyalkylbenzene, a solvent or promoter can be used.

Alkylation catalysts that are to be converted to compounds having an aromatic nucleus by olefins can be employed in the cyclization reaction. Examples include anhydrous aluminum chloride, boron trifluoride, hydrogen fluoride, phosphoric acid, sulfuric acid or solid acids such as silica/alumina or zeolite.

The amount of cyclization catalyst should be in the range of 0.5–20 weight % with respect to the 1:1 adduct. The solvent can be included at this stage of the process. The cyclization reaction proceeds nearly quantitatively. Upon the completion of the cyclization reaction, the cyclization catalyst is removed from the cyclization reaction products. Alkoxyalkyltetralin, the reaction product, is then separated by distillation in order to further supply reactants for the dehydrogenation reaction.

In principle, methods for dehydrogenation and aromatization for cyclohexane, cyclohexene or tetrahydronaphthalene can be applied to the dehydrogenation reaction of alkoxyalkyltetralin. For example, by heating alkoxyalkyltetralin in the presence of dehydrogenation catalysts such as noble metals, or sulfur or DDQ (2,3-dichoro- 5,6-dicyano-1,4-benzoquinone), the dehydrogenation of alkoxyalkyltetralin can be achieved through aromatization. It is, however, preferable to dehydrogenate alkoxyalkyltetralin by a reaction that takes place in the presence of catalysts such as noble metals. However, since the dehydrogenation reaction of alkoxyalkyltetralin is extremely difficult to control, it is necessary to select more active catalysts as well as appropriate reaction conditions.

Suitable catalysts for the dehydrogenation reaction include noble metals such as palladium, platinum or ruthenium. Moreover, they are supplied for use after being supported with the active carbon, alumina, or the like.

The alkoxyalkyltetralin used for the dehydrogenation reaction is not required to be highly pure provided catalytic poison is not included.

The dehydrogenation reaction of alkoxyalkyltetralin can be performed under either reduced pressure, atmospheric pressure or excess pressure by a batch process, semi-continuous process or continuous process in either a gaseous or liquid phase. When the dehydrogenation reaction is proceeded in the gaseous phase, the catalysts in which platinum, palladium, ruthenium or the like supported with active carbon or alumina is used. If a noble metal catalyst is supported with solid acid catalysts such as silica/alumina, cyclization and dehydrogenation reactions of the 1:1 adduct can be proceeded simultaneously.

The reaction temperature of the aforementioned dehyrogenation reaction lies in the range of 150°–300° C. in the case of the liquid phase reaction. Too high a reaction temperature is undesirable since hydrogenalysis will occur. In this case, including hydrogen acceptor compounds such as aromatic nitro compounds and/or solvents will provided better results.

Any non-inhibiting solvent which has a boiling point in a temperature ranging from 150° to 300° C. can generally be used in the dehydrogenation reaction. For example, alkane, cycloalkane or alkylaromatic compounds or alkoxyalkylbenzene which is a starting raw material can be utilized for this purpose.

For separation of the dehydrogenation reaction product, alkoxyalkylnaphthalene, from unreacted alkoxyalkyltetralin, any of the known separation techniques such as cooling precipitation, recrystallization, or distillation can be applied.

The yield can be enhanced by recycling unreacted alkoxyalkyltetralin which is separated and collected for reuse into the dehydrogenation reaction.

Side-reactions that could take place during the aforementioned dehydrogenation reaction, can be ignored if active catalysts are used, appropriate reaction conditions are selected, so that alkoxyalkylnaphthalene with a higher yield percentage with respect to alkoxyalkyltetralin can be obtained.

The thus obtained alkoxyalkylnaphthalene will be further subjected to an oxidation reaction, optionally after an isomerization reaction or substitutional reaction is completed.

The oxidation of alkoxyalkylnaphthalene can be performed by liquid phase air oxidation, liquid phase oxidation with reagent, or catalytic gaseous phase oxidation. For instance, in the case of liquid phase air oxidation, a low molecular weight fatty acid such as acetic acid, anhydrides thereof alone, or its mixture can be employed as a solvent. Furthermore, the oxidation can be performed by using one or more than two of catalyst group of heavy metals comprising cobalt, manganese, cerium, copper, palladium, ruthenium or the like, and at a reaction temperature range of 80°–200° C. In this case, if bromine or bromide are mixed in the catalyst system, the reaction rate as well as the yield can both be remarkably enhanced. Moreover, coexisting alkali metals such as sodium, potassium or the like will become higher the yield.

Moreover, the amount of reagents comsumed during the oxidation reaction of alkoxylalkylnaphthalene, can be reduced by liquid phase air oxidation under mild condition, namely at a reaction temperature ranging from 50° to 120° C. before completion of the reaction and then followed by liquid phase oxidation with reagent by using, for instance, nitric acid, chromic acid, hydrogen peroxide, peracetic acid, or the like.

Refining of alkoxynaphthalenecarboxylic acid which is produced by the oxidation reaction can be achieved by known techniques such as acid precipitation, crystallization or extraction methods which are adapted for these compounds.

EXAMPLES

Example 1

Into a 300 ml capacity flask that is provided with an electromagnetic stirrer were introduced o-methoxytoluene 1.0 mol, sodium 0.021 mol, potassium 0.014 mol and naphthalene 0.003 mol as a promoter. After the catalysts were dispersed by heating at a temperature of 110° C. while stirring, 1,3-butadiene was fed for 6 hours at a flow rate of 0.1 mol/hour. After completion of the addition reaction, water was added in order to deactivate the catalysts. The thus obtained reaction product was analyzed by gas chromatography. The results indicated that 5-(2-methoxyphenyl)-2-pentene was produced at a 64% yield with respect to the consumed o-methoxytoluene.

P-toluenesulfonic acid in the amount of 20 g was added to the reaction compounds to perform the cyclization reaction at a temperature of 160° C. for 5 hours with continuous stirring. After completion of the cyclization reaction, the reaction mixtures were neutralized by an aqueous solution of caustic soda equimoler to p-toluenesulfonic acid. After liquid separation, 5-methoxy-1-methyltetralin was quantitatively obtained.

The reaction mixtures were further distilled under a reflux ratio of 20 and a pressure of 50 mmHg in a distillation tower having 50 theoretical plates to recover 5-methoxy-1-methyltetralin with 90% yield.

100 g of the 5-methoxy-1-methyltetralin was then introduced into a three-necked flask, to which 10 g of active carbon supported with 10% ruthenium was added, and then heated by a mantle-heater for 100 hours while stirring by a glass stirrer. The vapor that had been generated during heating was recycled through a Liebig condenser to promote the dehydrogenation reaction. The results indicated that 5-methoxy-1-methylnaphthalene was produced at 50% conversion and 80% yield (with respect to the consumed 5-methoxy-1-methyltetralin).

After the thus obtained reaction product was filtered in order to remove the active carbon supported with ruthenium, it was further subjected to a process of distillation using a distillation tower with 50 theoretical plates under a reflux ratio of 20 and a pressure of 50 mmHg. This process in the described sequence yielded 5-methoxy-1-methylnaphthalene with 99.0% purity at a 93% recovery.

Into a titanium autoclave having a capacity of 500 ml were introduced the 5-methoxy-1-methylnaphthalene 5 g, in addition to cobalt acetate 0.015 mol, manganese bromide 0.015 mol, potassium bromide 0.015 mol and acetic acid 230 g and then heated to 140° C. by an electric furnace, and subjected to oxidation while stirring under a reaction pressure of 30 kg/cm$^2$ G while feeding air at a flow rate of 1 l/min until oxygen was no longer absorbed. It was found that 5-methoxy-1-naphthalenecarboxylic acid was obtained at 54% yield.

Example 2

Into a 300 ml capacity flask with an electromagnetic stirrer were introduced o-methoxytoluene 1.0 mol, sodium 0.021 mol, potassium 0.014 mol and naphthalene 0.003 mol as a promoter. After the flask was heated at a temperature of 110° C. while stirring to disperse the added catalysts, tetrahydrofuran 100 ml as a solvent was introduced at a temperature of 60° C. and 1,3-butadiene was added over a period of 6 hours at a flow rate of 0.1 mol/hour to promote the addition reaction. Analyses of the thus obtained reaction products done by gas chromatography indicated that 5-(2-methoxyphenyl)-2-pentene was obtained at an 60% yield with respect to the consumed o-methoxytoluene.

Example 3

Into a 300 ml capacity flask with an electromagnetic stirrer were introduced p-methoxytoluene 1.0 mol, sodium 0.021 mol, potassium 0.014 mol and naphthalene 0.003 mol as a promoter. After the flask was heated at a temperature of 110° C. while stirring to disperse the introduced catalysts, 1,3-butadiene was fed for 6 hours at a flow rate of 0.1 mol/hour. After completion of the reaction, water was added in order to deactivate and separate the catalyst. The thus obtained reaction product was analyzed by gas chromatography. The results indicated that 5-(4-methoxyphenyl)-2-pentene was produced at a 61% yield with respect to the consumed p-methoxytoluene.

20 g of p-toluenesulfonic acid was added to the obtained reaction compounds which was further subjected to the cyclization reaction, maintaining the reaction temperature at 160° C. for 5 hours while stirring. After the completion of the cyclization reaction, caustic soda aqueous solution equimoler to the p-toluenesulfonic acid was added in order to neutralize. After liquid separation, 7-methoxy-1-methyltetralin was quantitatively obtained.

The reaction compounds were further distilled in a distillation tower having 50 theoretical plates under a reflux ratio of 20 and a pressure of 50 mmHg to recover 7-methoxy-1-methyltetralin at a 90% yield.

100 g of the recovered 7-methoxy-1-methyltetralin was introduced into a flask having three necks and 10 g of active carbon supported with 10% ruthenium was added. The flask was then heating by a mantle-heater for 100 hours while stirring with a glass stirrer to promote the dehydrogenation reaction, while recycling the generated vapor through a Liebig condenser. It was found that 7-methoxy-1-methylnaphthalene was produced at 50% conversion and 80% yield (with respect to the consumed 7-methoxy-1-methyltetralin).

The thus obtained reaction product was further filtered in order to remove the active carbon that had been carried on the ruthenium and then distilled using a distillation tower with the 50 theoretical plates under a reflux ratio of 20 and a pressure of 50 mmHg. It was found that by using the previously described reaction sequence 99.0% pure 7-methoxy-1-methylnaphthalene was obtained at 94% yield.

The 7-methoxy-1-methylnaphthalene, 5 g, cobalt acetate 0.015 mol, manganese acetate 0.015 mol, potassium bromide 0.015 mol and acetic acid 230 g were then introduced into a titanium autoclave with a 500 ml capacity. The autoclave was heated up to 140° C. by an electric furnace, and was subjected to oxidation while stirring under a reaction pressure of 30 kg/cm$^2$ G while feeding air at a flow rate of 1 l/min until the oxygen was no longer absorbed. It was found that 7-methoxy-1-naphthalenecarboxylic acid was produced at 65% yield in this manner.

Example 4

Into a 500 ml capacity flask with an electromagnetic stirrer were introduced m-methoxytoluene 3.0 mol, sodium 0.063 mol, potassium 0.042 mol and naphthalene 0.009 mol as a promoter.

After the flask was heated at a temperature of 110° C. during stirring in order to disperse the catalysts, 1,3-butadiene was fed for 6 hours at a flow rate of 0.3 mol/hour in order to promote the addition reaction. After the completion of the reaction, water was added to deactivate and separate the catalysts. The thus obtained reaction mixture was analyzed by gas chromatography. The results indicated that 5-(3-methoxyphenyl)-2-pentene was produced at 79% yield with respect to the consumed m-methoxytoluene.

12 g of silica/alumina catalyst (Nikki Chemical N633L) was added to the reaction mixture. The cyclization was then carried out at 200° C. for 3 hours while stirring. The reaction products were analyzed by gas chromatography. The results indicated that 6-methoxy-1-methyltetralin was produced at a 48% yield.

After the reaction products were filtered to remove the used silica/alumina catalysts, the reaction products were then distilled in a distillation tower having 50 theoretical plates under a reflux ratio of 20 and a pressure of 50 mmHg to recover 6-methoxy-1-methyltetralin at 85% yield (with respect to the consumed 6-methoxy-1-methyltetralin).

100 g of the recovered 6-methoxy-1-methyltetralin was placed in a flask having three necks. 100 g of m-methoxytoluene acting as a solvent and active carbon 2 g supported with 10% palladium were added. The flask was then heated by a mantle-heater at a temperature of 200° C. for 24 hours while stirring with a glass stirrer to promote the dehydrogenation reaction, while recycling the generated vapor through a Liebig condenser. It was found that 6-methoxy-1-methylnaphthalene was produced at 92% conversion and 90% yield (with respect to the consumed 6-methoxy-1-methyltetralin) in this sequence.

The thus obtained reaction products were further filtered to remove the active carbon supported with the palladium, and distilled off to remove the solvent m-methoxytoluene to obtain 6-methoxy-1-methylnaphthalene.

20 g of the 6-methoxy-1-methylnaphthalene, cobalt acetate 0.020 mol, potassium bromide 0.015 mol and acetic acid 230 g were introduced into a 500 ml capacity titanium autoclave. The autoclave was heated up to 100° C. by an electric furnace, and the contents subjected to oxidation while stirring, under a reaction pressure of 30 kg/cm²G while feeding air at a flow rate of 1 l/min until the oxygen was no longer absorbed. It was found that 6-methoxy-1-naphthalenecarboxylic acid was produced at 82% yield.

Example 5

6-methoxy-1-methyltetralin in the amount of 100 g, which was recovered in example 4, was placed in a flask having three necks to which 1,2,4-trimethylbenzene 100 g acting as a solvent and active carbon 2 g supported with 10% palladium were added. The flask was heated at a temperature of 200° C. by a mantle-heater for 24 hours while stirring with a glass stirrer. The vapor generated was condensed and recycled through a Liebig condenser to promote the dehydrogenation reaction. It was found that 6-methoxy-1-methylnaphthalene was produced at 92% conversion and 90% yield (with respect to the consumed 6-methoxy-1-methyltetralin).

From the foregoing reactions performed in accordance with to the present invention, alkoxynaphthalenecarboxylic acid, which is known to be difficult to produce by the Kolbe-Schmitt process using naphthol, can be produced and continuously supplied as an intermediate raw material for use in various field of medicine, agricultural chemicals, resins, electronic materials, and the like. Moreover, alkoxyalkyltetralin and alkoxyalkylnaphthalene can also be produced at an intermediate stage of the process.

While this invention has been explained with reference to the process described herein, it is not confined to the details as set forth and this application is intended to cover any modifications and changes as may come within the scope of the following claims.

We claim:

1. A method for producing alkoxyalkyltetralin comprising the steps of:

in a presence of an alkali metal catalyst adding 1,3-butadiene to an alkoxyalkylbenzene having the formula

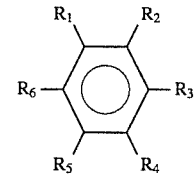

wherein

R₁ is alkyl group having a benzylic hydrogen;

R₂ through R₆ are H, alkyl, phenyl, alkoxy, or phenoxy, and either of R₂ and R₆ is H, and at least one of R₂ through R₆ is alkoxy or phenoxy, to yield an adduct; and subjecting said adduct to cyclization in a presence of an acid catalyst to yield alkoxyalkyltetralin.

2. The method according to claim 1, wherein said step of adding 1,3-butadiene is performed in a presence of a promoter selected from the group consisting of naphthalene, biphenyl, phenanthrene, anthracene, pyrene, and an alkyl derivative thereof.

3. The method according to claim 1, wherein said alkali metal catalyst is dissolved in an ether selected from the group consisting of diethyl ether, tetrahydrofuran, and dioxane.

4. The method according to claim 1, wherein said acid catalyst is selected from the group consisting of anhydrous aluminum chloride, boron trifluoride, hydrogen fluoride, phosphoric acid, sulfuric acid, silica/alumina and zeolite.

5. The method according to claim 1, further comprising the step of dehydrogenating said alkoxyalkyltetralin to yield alkoxyalkylnaphthalene.

6. The method according to claim 5, wherein said step of dehydrogenating is performed in a presence of a dehydrogenation catalyst selected from the group of a noble metal, sulfur, 2,3-dichloro-5,6-dicyano-1,4-benzoquinone.

7. The method according to claim 6, wherein said noble metal is palladium, platinum or ruthenium.

8. The method according to claim 6, wherein said noble metal is supported with an active carbon or alumina.

9. The method according to claim 8, wherein said steps of dehydrogenating and subjecting to cyclization are performed simultaneously.

10. The method according to claim 5, further comprising the step of oxidizing said alkoxyalkylnaphthalene to yield alkoxynaphthalenecarboxylic acid.

11. A method for producing alkoxyalkyltetralin comprising the steps of:

in a presence of an alkali metal catalyst adding 1,3-butadiene to an alkoxyalkylbenzene having the formula

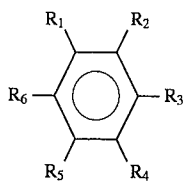

wherein $R_1$ is alkyl group having a benzylic hydrogen;

$R_2$ through $R_6$ are H, alkyl, phenyl, alkoxy, or phenoxy, and either of $R_2$ and $R_6$ is H, and at least one of $R_2$ through $R_6$ is alkoxy or phenoxy, and in a presence of a promoter selected from the group consisting of naphthalene, biphenyl, phenanthrene, anthracene, pyrene, and an alkyl derivative thereof to yield an adduct; and subjecting said adduct to cyclization in a presence of an acid catalyst to yield alkoxyalkyltetralin.

12. The method according to claim 11, further comprising the step of dehydrogenating said alkoxyalkyltetralin to yield alkoxyalkylnaphthalene in a presence of a dehydrogenation catalyst selected from the group of a noble metal, sulfur, 2,3-dichloro-5,6-dicyano-1,4-benzoquinone.

13. The method according to claim 12, wherein said noble metal is palladium platinum or ruthenium, and said noble metal is supported with an active carbon or alumina.

14. The method according to claim 13, further comprising the step of oxidizing said alkoxyalkylnaphthalene to yield alkoxynaphthalenecarboxylic acid.

15. The method according to claim 12 further comprising the step of oxidizing said alkoxyalkylnaphthalene to yield alkoxynaphthalenecarboxylic acid.

* * * * *